(12) United States Patent
Godrich et al.

(10) Patent No.: US 11,544,849 B2
(45) Date of Patent: Jan. 3, 2023

(54) SYSTEMS AND METHODS TO PROCESS ELECTRONIC IMAGES TO CATEGORIZE INTRA-SLIDE SPECIMEN TISSUE TYPE

(71) Applicant: PAIGE.AI, Inc., New York, NY (US)

(72) Inventors: Ran Godrich, New York, NY (US); Christopher Kanan, Pittsford, NY (US)

(73) Assignee: PAIGE.AI, Inc., New York, NY (US)

( * ) Notice: Subject to any disclaimer, the term of this patent is extended or adjusted under 35 U.S.C. 154(b) by 0 days.

(21) Appl. No.: 17/646,513

(22) Filed: Dec. 30, 2021

(65) Prior Publication Data

US 2022/0375071 A1 Nov. 24, 2022

Related U.S. Application Data

(63) Continuation of application No. 17/646,500, filed on Dec. 30, 2021.
(Continued)

(51) Int. Cl.
*G06T 7/00* (2017.01)
*G06T 7/194* (2017.01)
(Continued)

(52) U.S. Cl.
CPC ......... *G06T 7/0012* (2013.01); *G06N 3/0472* (2013.01); *G06T 7/194* (2017.01);
(Continued)

(58) Field of Classification Search
None
See application file for complete search history.

(56) References Cited

U.S. PATENT DOCUMENTS

2019/0080450 A1* 3/2019 Arar ................. G06T 7/194
2020/0372635 A1 11/2020 Veidman et al.
(Continued)

OTHER PUBLICATIONS

Le Hou et al: "Patch-Based Convolutional Neural Network for Whole Slide Tissue Image Classification", Mar. 9, 2016 (Mar. 9, 2016), XP055523985, Retrieved from the Internet: URL:https://arxiv.org/pdf/1504.07947.pdf [retrieved on Nov. 14, 2018].

*Primary Examiner* — Samah A Beg
(74) *Attorney, Agent, or Firm* — Bookoff McAndrews, PLLC

(57) ABSTRACT

Systems and methods are disclosed for identifying tissue specimen types present in digital whole slide images. In some aspects, tissue specimen types may be identified using unsupervised machine learning techniques for out-of-distribution detection. For example, a digital whole slide image of a tissue specimen and a recorded tissue specimen type for the digital whole slide image may be received. One or more feature vectors may be extracted from one or more foreground tiles of the digital whole slide image identified as including the tissue specimen, and a distribution learned by a machine learning system for the recorded tissue specimen type may be received. Using the distribution, a probability of the feature vectors corresponding to the recorded tissue specimen type may be computed and used as a basis for classifying the foreground tiles from which the feature vectors are extracted as an in-distribution foreground tile or an out-of-distribution foreground tile.

20 Claims, 12 Drawing Sheets

Related U.S. Application Data

(60) Provisional application No. 63/191,729, filed on May 21, 2021.

(51) Int. Cl.
*G06N 3/04* (2006.01)
*G06T 7/11* (2017.01)

(52) U.S. Cl.
CPC ....... *G06T 7/11* (2017.01); *G06T 2207/20081* (2013.01); *G06T 2207/20084* (2013.01); *G06T 2207/30024* (2013.01)

(56) References Cited

U.S. PATENT DOCUMENTS

| | | | |
|---|---|---|---|
| 2021/0350176 A1* | 11/2021 | Klaiman | G06V 10/40 |
| 2022/0101519 A1* | 3/2022 | Yip | G06T 1/20 |

* cited by examiner

SYSTEMS AND METHODS TO PROCESS ELECTRONIC IMAGES TO CATEGORIZE INTRA-SLIDE SPECIMEN TISSUE TYPE

RELATED APPLICATION(S)

This application is a continuation of and claims priority to U.S. Non-provisional application Ser. No. 17/646,500 filed on Dec. 30, 2021, which claims priority to U.S. Provisional Application No. 63/191,729 filed May 21, 2021, the entire disclosures of which are hereby incorporated by reference in their entireties.

FIELD OF THE DISCLOSURE

Various embodiments of the present disclosure pertain generally to image processing methods. More specifically, particular embodiments of the present disclosure relate to systems and methods for processing electronic images to categorize (e.g., classify) intra-slide specimen tissue type.

BACKGROUND

When processing a digitized image of a slide-mounted histopathology specimen (e.g., a digital whole slide image), it is often assumed that there is only a single tissue specimen type present in the slide as indicated by a database, such as a laboratory information system. However, in some instances, the recorded tissue specimen type in the laboratory information system may be erroneous and/or one or more additional tissue specimen types may be present in the slide that are not recorded in the laboratory information system. Not only does this result in inaccurate recording, but may also cause an incorrect application of an artificial intelligence (AI)-based image processing system specific to a given tissue specimen type to one or more regions of the digital whole slide image that include a different tissue specimen type.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for processing electronic images to categorize intra-slide tissue specimen type.

A system for identifying tissue specimen types present in digital whole slide images may be described. The system may include a processor and a memory coupled to the processor and storing instructions that, when executed by the processor, cause the processor to perform operations. The operations may include receiving a digital whole slide image of a tissue specimen and a tissue specimen type recorded for the digital whole slide image, identifying one or more foreground tiles of the digital whole slide image comprising the tissue specimen, extracting one or more feature vectors from the one or more foreground tiles, and receiving a distribution learned by a machine learning system for the tissue specimen type recorded for the digital whole slide image. The operations may further include determining, using the distribution, a probability of the one or more feature vectors corresponding to the tissue specimen type recorded for the digital whole slide image, and based on the probability, classifying the one or more foreground tiles from which the one or more feature vectors are extracted as one of an in-distribution foreground tile or an out-of-distribution foreground tile.

A method for identifying tissue specimen types present in digital whole slide images may be described. The method may include receiving a digital whole slide image of a tissue specimen and a tissue specimen type recorded for the digital whole slide image, identifying one or more foreground tiles of the digital whole slide image comprising the tissue specimen, extracting one or more feature vectors from the one or more foreground tiles, and receiving a distribution learned by a machine learning system for the tissue specimen type recorded for the digital whole slide image. The method may further include determining, using the distribution, a probability of the one or more feature vectors corresponding to the tissue specimen type recorded for the digital whole slide image, and based on the probability, classifying the one or more foreground tiles from which the one or more feature vectors are extracted as one of an in-distribution foreground tile or an out-of-distribution foreground tile.

A non-transitory computer-readable medium may store instructions that, when executed by a processor, cause the processor to perform operations for identifying tissue specimen types present in digital whole slide images may be described. The operations may include receiving a digital whole slide image of a tissue specimen and a tissue specimen type recorded for the digital whole slide image, identifying one or more foreground tiles of the digital whole slide image comprising the tissue specimen, extracting one or more feature vectors from the one or more foreground tiles, and receiving a distribution learned by a machine learning system for the tissue specimen type recorded for the digital whole slide image. The operations may further include determining, using the distribution, a probability of the one or more feature vectors corresponding to the tissue specimen type recorded for the digital whole slide image, and based on the probability, classifying the one or more foreground tiles from which the one or more feature vectors are extracted as one of an in-distribution foreground tile or an out-of-distribution foreground tile.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated into and constitute a part of this specification, illustrate various exemplary embodiments and together with the description, serve to explain the principles of the disclosed embodiments.

DESCRIPTION OF THE EMBODIMENTS

Figure 1A:
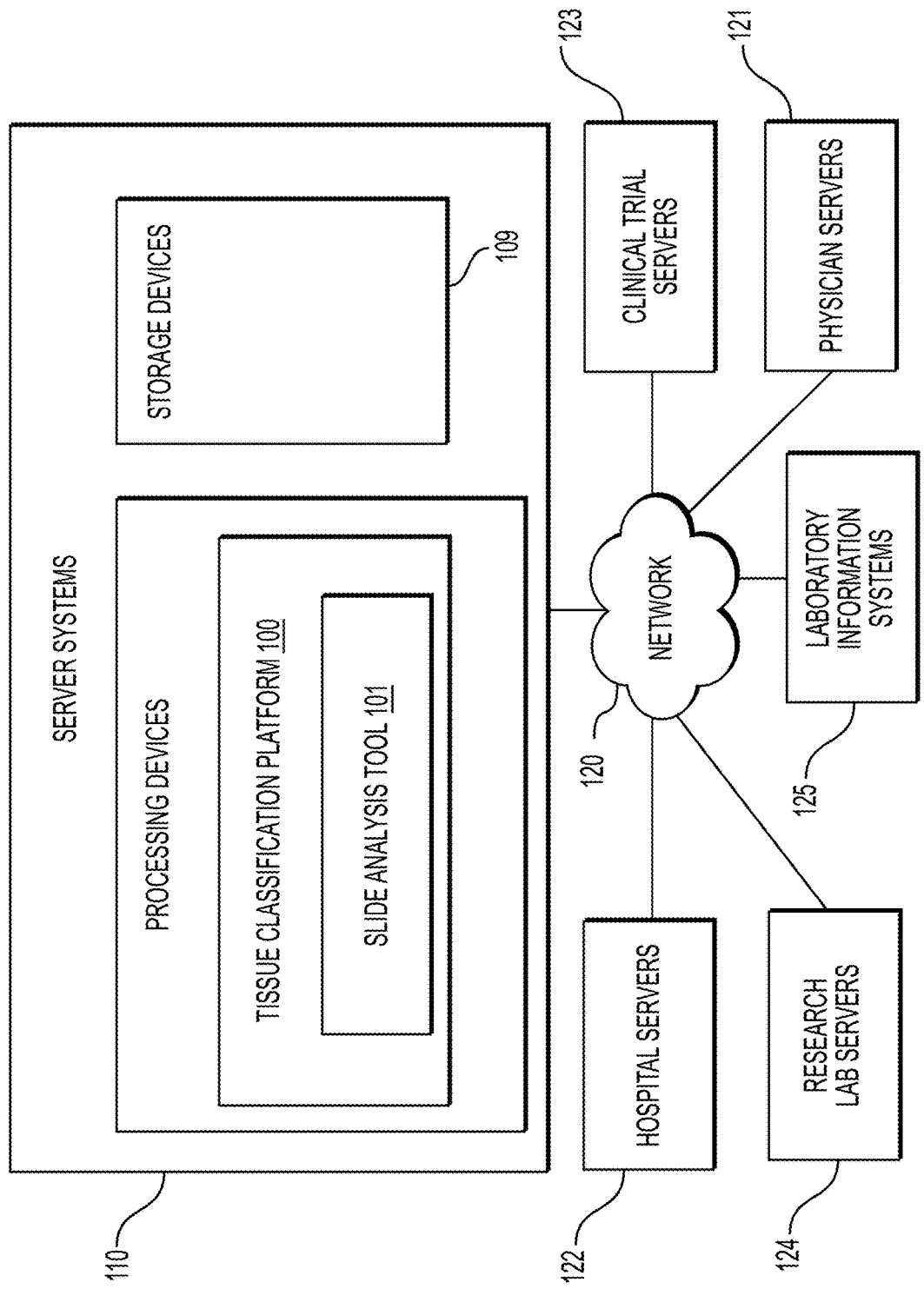
FIG. 1A illustrates an exemplary block diagram of a system and network to classify one or more tissue specimen types present in digital whole slide images, according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

In histopathology, a slide often has a single tissue specimen type, such as a breast tissue specimen removed during a breast lumpectomy, and this tissue specimen type may be indicated or recorded in a laboratory information system as the tissue specimen type for the slide. However, in some scenarios, the physical tissue specimen may contain more than the single tissue type specified in the laboratory information system and/or data within the laboratory information system may be inconsistent with one or more tissue specimen types that are actually on the slide. As one illustrative example, in a bladder resection, a portion of prostate tissue may also be extracted during the resection, resulting in a slide that may include both bladder tissue and prostate tissue. As another illustrative example, a patient may have a tumor excised along with one or more lymph nodes to identify metastasis, and a slide may be prepared that contains both the tumor and lymph nodes. Additionally and/or alternatively, data within the laboratory information system may be incorrect. For example, slides prepared with specimen from a liver biopsy performed to identify metastasis to the liver of a cancer originating in a different tissue type may be incorrectly recorded as liver tissue being the primary tumor type. Data within the laboratory information system may also be incomplete because it does not contain a full description of each tissue type when there are multiple tissue specimen types present within a slide or a collection of slides in a part specimen.

When the tissue specimen type within a slide is heterogeneous and/or is recorded incorrectly, pathologists operating on this data may not be able to retrieve the necessary information to look up the specimen. Additionally and/or alternatively, an AI system that is specific to the tissue type recorded may be run on the digitized image of the slide, resulting in erroneous outputs due to the heterogeneity of tissue specimen types and/or incorrect recording of tissue specimen type in the image. For example, if a liver tissue specimen was erroneously recorded as a breast tissue specimen in a laboratory information system, a breast tissue-specific AI system (e.g., model, algorithm, system, architecture, etc.) may be incorrectly executed to process the image of the liver tissue specimen, resulting in erroneous outputs.

Aspects disclosed herein solve these problems by using trained machine learning systems, AI, and/or image processing techniques on digital whole slide images of histopathology specimens to classify tissue specimen types present at one or more locations or regions on the slide. By classifying intra-slide tissue type(s), mismatches with data recorded in informational databases and/or subsequent application of incorrect tissue type-specific AI systems may be mitigated.

The Environment

FIG. 1A illustrates an exemplary block diagram of a system and network to classify one or more tissue specimen types present in digital whole slide images, according to an exemplary embodiment of the present disclosure.

Specifically, FIG. 1A illustrates an electronic network 120 that may be connected to servers at hospitals, laboratories, and/or doctor's offices, etc. For example, physician servers 121, hospital servers 122, clinical trial servers 123, research lab servers 124, and/or laboratory information systems 125, etc., may each be connected to electronic network 120, such as the Internet, through one or more computers, servers and/or handheld mobile devices. According to an exemplary embodiment of the present application, electronic network 120 may also be connected to server systems 110, which may include processing devices that are configured to implement a tissue classification platform 100, which includes a slide analysis tool 101 for using machine learning, AI, and/or image processing tools to identify one or more tissue specimen types present in digital whole slide images, according to an exemplary embodiment of the present disclosure.

Physician servers 121, hospital servers 122, clinical trial servers 123, research lab servers 124 and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof (referred to herein collectively as digital whole slide images). Physician servers 121, hospital servers 122, clinical trial servers 123, research lab servers 124 and/or laboratory information systems 125 may also obtain any combination of patient-specific information, such as age, medical history, cancer treatment history, family history, past biopsy or cytology information, etc. Physician servers 121, hospital servers 122, clinical trial servers 123, research lab servers 124 and/or laboratory information systems 125 may transmit digitized slide images and/or patient-specific information to server systems 110 over the electronic network 120. Laboratory information systems 125 may also store data associated with the digital whole slide images, such as tissue specimen types recorded as being included in the respective images that may be transmitted along with the digital whole slide images to server systems 110 over network 120.

Server systems 110 may include one or more storage devices 109 for storing images and data received from at least one of physician servers 121, hospital servers 122, clinical trial servers 123, research lab servers 124, and/or laboratory information systems 125. Server systems 110 may also include processing devices for processing images and data stored in the one or more storage devices 109. Server systems 110 may further include one or more machine learning tool(s) or capabilities. For example, the processing devices may include one or more machine learning tools for tissue classification platform 100, according to one embodiment. Alternatively or in addition, the present disclosure (or portions of the system and methods of the present disclosure) may be performed on a local processing device (e.g., a laptop).

Physician servers 121, hospital servers 122, clinical trial servers 123, research lab servers 124 and/or laboratory information systems 125 refer to systems used by pathologists for reviewing the digital whole slide images. As previously discussed, tissue type information associated with the digital whole slide images may be stored in a laboratory information system 125.

Figure 1B:
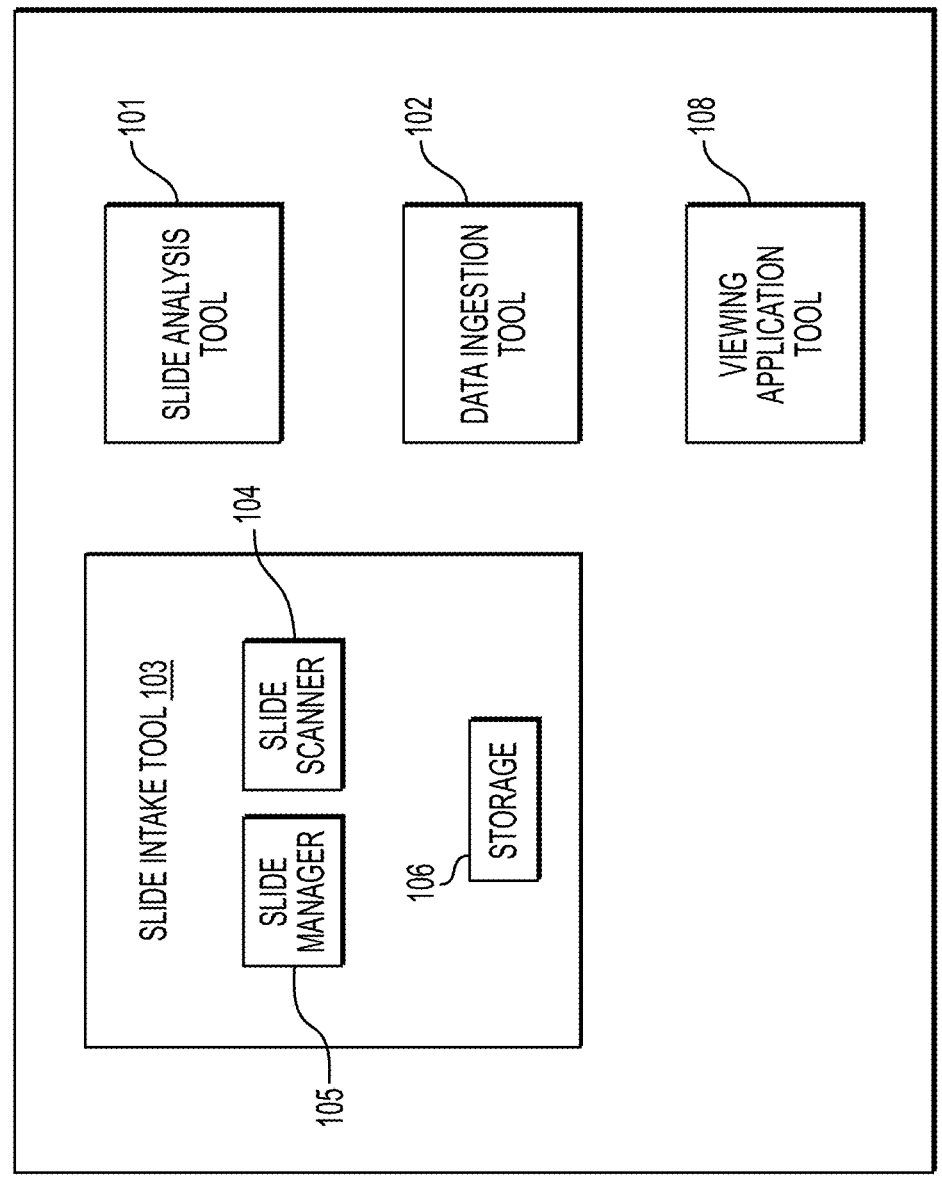
FIG. 1B illustrates an exemplary block diagram of a tissue classification platform, according to an exemplary embodiment of the present disclosure.

FIG. 1B illustrates an exemplary block diagram of tissue classification platform 100. Tissue classification platform 100 may include a slide analysis tool 101, a data ingestion tool 102, a slide intake tool 103, a slide scanner 104, a slide manager 105, a storage 106, and a viewing application tool 108.

Slide analysis tool 101, as described below, refers to a process and system for identifying one or more tissue specimen types present in digital whole slide images. Unsupervised and/or supervised machine learning techniques may be implemented in conjunction with image processing techniques to identify the tissue specimen types.

Data ingestion tool 102 may facilitate a transfer of the digital whole slide images to the various tools, modules, components, and devices that are used for classifying and processing the whole slide images, according to an exemplary embodiment. The slide intake tool 103 may scan pathology slides and convert them into a digital form, according to an exemplary embodiment. The slides may be scanned with slide scanner 104, and the slide manager 105 may process the images on the slides into digital whole slide images and store the digital whole slide images in storage 106. Viewing application tool 108 may provide a user (e.g., a pathologist) a user interface that displays the digital whole slide images. The user interface may also display one or more indications of the tissue specimen types identified and/or notification or alerts (e.g., if there is a discrepancy between the tissue specimen types identified and the tissue specimen types recorded in laboratory information system 125). The information may be provided through various output interfaces (e.g., a screen, a monitor, a storage device and/or a web browser, etc.).

Slide analysis tool 101, and one or more of its components, may transmit and/or receive digital whole slide images and/or patient information to server systems 110, physician servers 121, hospital servers 122, clinical trial servers 123, research lab servers 124, and/or laboratory information systems 125 over an electronic network 120. Further, server systems 110 may include storage devices for storing images and data received from at least one of slide analysis tool 101, data ingestion tool 102, slide intake tool 103, slide scanner 104, slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively, or in addition, the present disclosure (or portions of the system and methods of the present disclosure) may be performed on a local processing device (e.g., a laptop).

Any of the above devices, tools and modules may be located on a device that may be connected to an electronic network such as the Internet or a cloud service provider, through one or more computers, servers and/or handheld mobile devices.

Figure 1C:
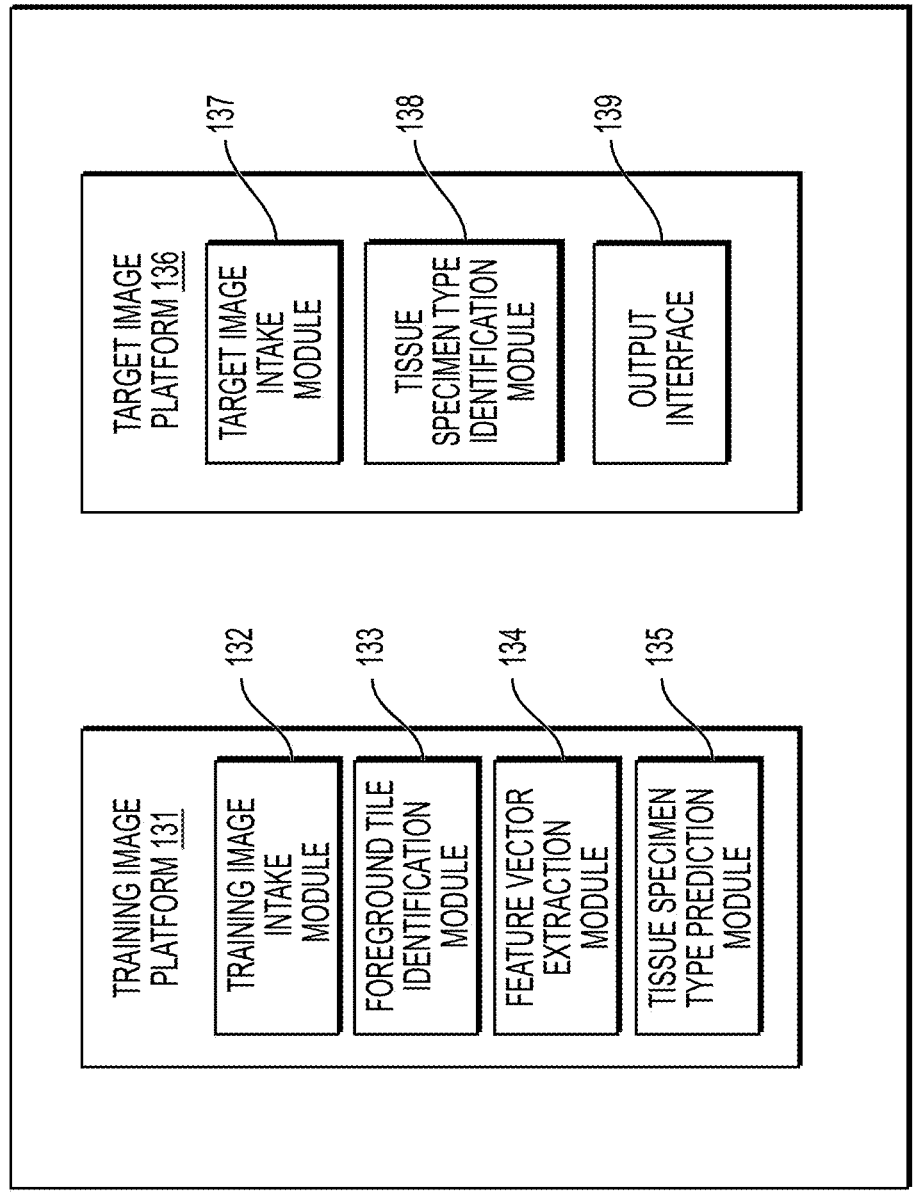
FIG. 1C illustrates an exemplary block diagram of a slide analysis tool, according to an exemplary embodiment of the present disclosure.

FIG. 1C illustrates an exemplary block diagram of slide analysis tool 101, according to an exemplary embodiment of the present disclosure. Slide analysis tool 101 may include a training image platform 131 and/or a target image platform 136.

According to one embodiment, training image platform 131 may include a plurality of software modules, including a training image intake module 132, a foreground tile identification module 133, a feature vector extraction module 134, and a tissue specimen type prediction module 135.

Training image platform 131, according to one embodiment, may create or receive one or more datasets of training images used to generate and train one or more machine learning systems that, when implemented, facilitate identification of one or more tissue specimen types present in one or more locations or regions of digital whole slide images. For example, the training images may include digital whole slide images received from any one or any combination of server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Example digital whole slide images may include digitized images of slide-mounted pathology specimens.

The training image intake module 132 of the training image platform 131 may create or receive the one or more datasets of training images. For example, the datasets may include a plurality of digital whole slide images for each of a variety of tissue specimen types to enable tissue type identification across a multitude of different tissue specimen types. For example, one dataset may include a plurality of digital whole slide images of breast tissue specimens, another dataset may include a plurality of digital whole slide images of liver tissue specimens, a further dataset may include a plurality of digital whole slide images of prostate tissue specimens, and so on. In some examples, annotations corresponding to the training images may also be received as part of the datasets, where the annotations label the known tissue specimen types present in the training images. In some examples, the annotations may be strong annotations that label tissue specimen type at a pixel level within the training images. In other examples, the annotations may be weak annotations that label tissue specimen type at an image or specimen level. The datasets may be stored on a digital storage device (e.g., one of storages devices 109).

A digital whole slide image of tissue specimen may be comprised of a plurality of tiles, where a first portion of the tiles may include foreground tiles and a second portion of the tiles may include background tiles. The foreground tiles may include the locations or regions of the digital whole slide image comprising the tissue specimen. Foreground tile identification module 133 may identify foreground tiles within the digital whole slide images received as training images using one or more image processing techniques. Feature vector extraction module 134 may extract one or more features, for placement into a vector, (e.g., a feature vector) from each of the foreground tiles identified by foreground tile identification module 133. In some aspects, one or more machine learning systems may be generated and trained to enable the feature extraction, as described in more detail below with reference to FIG. 2. Tissue specimen type prediction module 135 may generate, using at least the extracted feature vectors for the foreground tiles of the training images, one or more machine learning systems for predicting a tissue specimen type included in one or more locations or regions (e.g., in one or more foreground tiles) of a digital whole slide image. In some examples, the machine learning systems may be supervised machine learning systems and the corresponding annotations for the training images may also be used as part of the generation and training process. In other examples, the machine learning systems may be unsupervised machine learning systems. According to one aspect, a machine learning system may be generated for each tissue specimen type (e.g., tissue type-specific machine learning systems may be generated). According to another aspect, one machine learning system may be generated that is capable of tissue specimen type identification across a variety of different tissue specimen types.

According to one embodiment, target image platform 136 may include software modules, such as a target image intake module 137 and a tissue specimen type identification module 138, in addition to an output interface 139. Target image platform 136 may receive, as a target image input, a digital whole slide image of a tissue specimen via target image intake module 137. For example, the digital whole slide image may be received from any one or any combination of server systems 110, physician servers 121, hospital servers 122, clinical trial servers 123, research lab servers 124, and/or laboratory information systems 125. The digital whole slide image may be provided to tissue specimen type identification module 138 to identify one or more tissue specimen types present in the digital whole slide image. Tissue specimen type identification module 138 may be comprised of one or more sub-modules, including foreground tile identification module 133, feature vector extraction module 134, and tissue specimen type prediction module 135. Tissue specimen type identification module 138 may execute the one or more machine learning systems generated by the training image platform 131 to facilitate the identification of a tissue specimen type present in one or more locations or regions (e.g., within foreground tiles) of the digital whole slide image.

The output interface 139 may be used to output the adjusted target whole slide image (e.g., to a screen, monitor, storage device, web browser, etc.).

Figure 2:
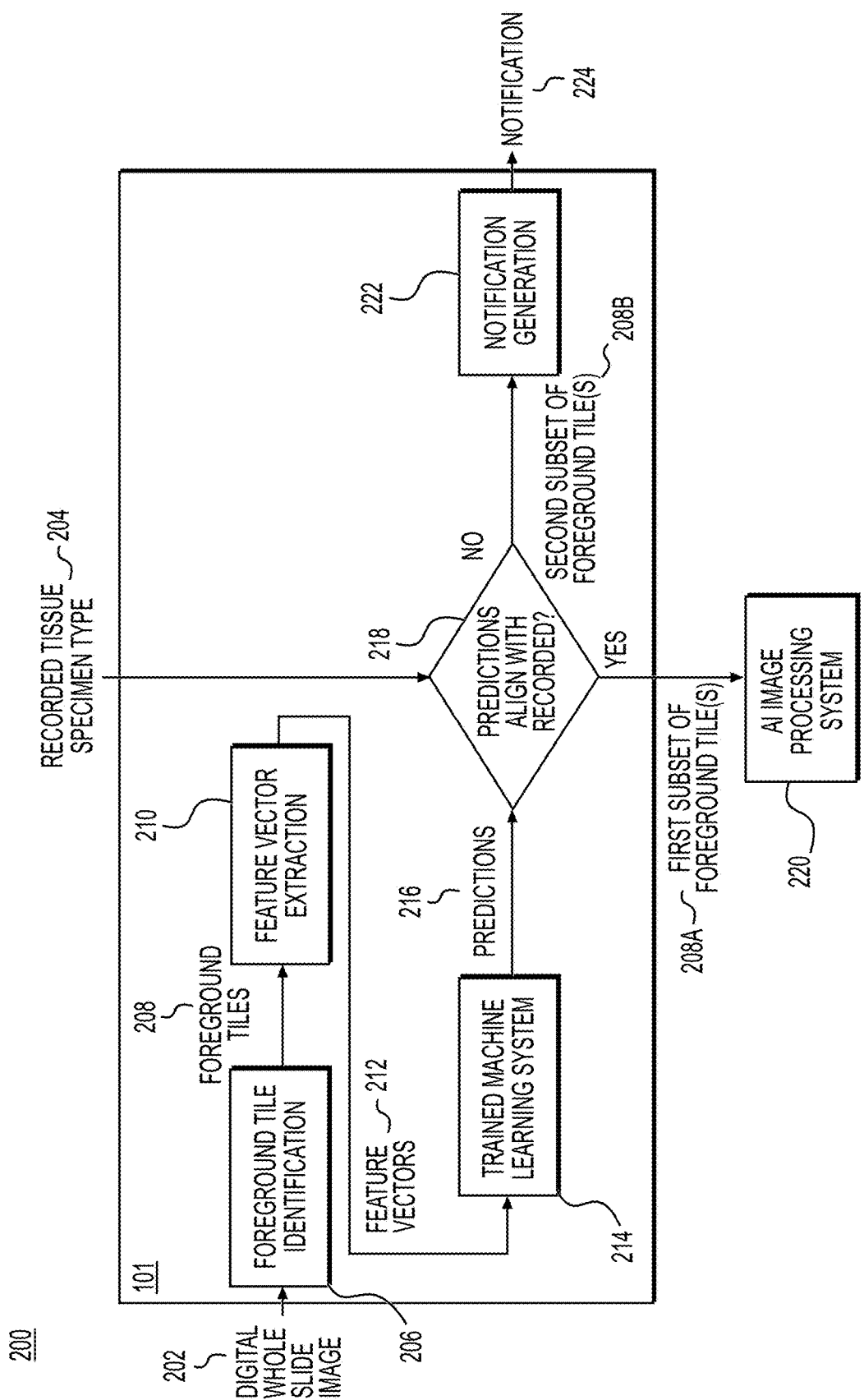
FIG. 2 is a flow diagram illustrating an exemplary process for using a trained machine learning system to identify one or more tissue specimen types present in a digital whole slide image, according to an exemplary embodiment of the present disclosure.

FIG. 2 is a flow diagram illustrating an exemplary process 200 for using a machine learning system to identify one or more tissue specimen types present in a digital whole slide image, according to an exemplary embodiment of the present disclosure. Exemplary process 200 may be performed by target image platform 136 of slide analysis tool 101 automatically and/or in response to a request from a user (e.g., pathologist, patient, oncologist, technician, administrator, etc.).

Exemplary process 200 may include receiving a digital whole slide image 202 of a tissue specimen as input to slide analysis tool 101. Digital whole slide image 202 may be a digitized image of a slide-mounted tissue specimen received from physician servers 121, hospital servers 122, clinical trial servers 123, research lab servers 124 and/or laboratory information systems 125 and stored in one of storage devices 109. A recorded tissue specimen type 204 for digital whole slide image 202 may also be received as input to slide analysis tool 101. Recorded tissue specimen type 204 may be received from laboratory information systems 125 or other similar databases storing information, including tissue type information, in association with a plurality of digital whole slide images, including digital whole slide image 202. Digital whole slide image 202 may be comprised of a plurality of tiles, including foreground tiles and background tiles, and each of the tiles may be comprised of a plurality of pixels. The foreground tiles may include locations or regions of digital whole slide image 202 that include the tissue specimen.

At step 206, process 200 may include identifying one or more foreground tiles 208 of digital whole slide image 202 including the tissue specimen. Discrimination between foreground and background tiles of digital whole slide image 202 may be performed using any one of a variety of image processing techniques. In one example, thresholding based on a variance of pixels within a given tile may be implemented to identify whether the given tile is a foreground tile. In another example, Otsu's method (e.g., a type of automatic image thresholding that separates pixels into two classes, foreground and background) may be performed. In a further example, pixel values of a given tile may be compared to a reference foreground distribution.

In step 210, process 200 may include extracting feature vectors 212 from the foreground tiles 208. A feature vector for a given foreground tile may be a vector representing one or more features of the given foreground tile. The extraction may be performed using one of a variety of image processing and/or machine learning techniques. In one example, hand-engineered features, such as descriptors including a scale-invariant feature transform (SIFT) descriptor, an Oriented FAST and rotated BRIEF (ORB) feature, a radiant-invariant feature transform (RIFT) descriptor and/or a speeded up robust features (SURF) descriptor, may be generated for a given foreground tile and converted into the feature vector for the given tile. In another example, the extracted feature vector may be a convolutional neural network (CNN) embedding, the CNN trained using supervised and/or self-supervised learning techniques. In a further example, the feature vector may be extracted using a trained transformer neural network. In a yet further example, the feature may be extracted using an original, unaltered pixel patch.

Feature vectors 212 may then be provided as input to a trained machine learning system 214 for predicting tissue specimen types. Each of feature vectors 212 may be input and run individually by trained machine learning system 214. In some examples, trained machine learning system 214 may be an unsupervised machine learning system, as described below with references to FIGS. 3A and 3B. In other examples, trained machine learning system 214 may be a supervised machine learning system, as described below with reference to FIGS. 4A and 4B. Trained machine learning system 214 may be one of the machine learning systems generated and trained by training image platform 131 of slide analysis tool 101. Alternatively, the machine learning system may be generated and/or trained by a third party and provided to systems 110 for execution by target image platform 136 of slide analysis tool 101. Additionally, in some examples, trained machine learning system 214 may be selected based on (e.g., is trained specifically for) recorded tissue specimen type 204.

Predictions 216 associated with a tissue specimen type present in the respective foreground tiles 208 from which the feature vectors 212 are extracted may be received as output from trained machine learning system 214. In some examples, predictions 216 may be a probability that the tissue specimen type of the tissue specimen included in the respective foreground tiles 208 from which the feature vectors 212 are extracted is (e.g., matches or aligns with) recorded tissue specimen type 204. In other examples, predictions 216 may include tissue specimen type classifications identifying a tissue specimen type predicted for the tissue specimen included in the respective foreground tiles 208. Predictions 216 may include a prediction for each of foreground tiles 208 of digital whole slide image 202 provided as input to collectively represent a predicted one or more tissue specimen types present in an entirety of digital whole slide image 202. In some examples, digital whole slide image 202 may be displayed through a user interface of viewing application tool 108 along with one or more indicators labeling respective foreground tiles 208 with associated predictions 216 in the displayed digital whole slide image 202.

In step 218 of process 200, predictions 216 may be compared to recorded tissue specimen type 204 to determine whether predictions 216 align with recorded tissue specimen type 204. Based on the comparison, predictions 216 for at least a subset of foreground tiles (e.g., first subset of foreground tiles 208A) may be determined to align or match with recorded tissue specimen type 204. In response to determining such alignment, first subset of foreground tiles 208A may be provided to an AI image processing system 220 that is specific to the recorded tissue specimen type for processing. For example, AI image processing system 220 may predict a presence and/or type of a condition or disease associated with the recorded tissue specimen type for diagnostics (e.g., a breast tissue-specific AI image processing system may determine a presence and/or type of breast cancer).

Additionally and/or alternatively, based on the comparison, a discrepancy may be determined between predictions 216 and recorded tissue specimen type 204 for at least a subset of foreground tiles (e.g., a second subset of foreground tiles 208B). In response to determining the discrepancy, at step 222 of process 200, a notification 224 indicating the discrepancy may be generated. The discrepancy may be a mismatch between a tissue specimen type predicted and recorded tissue specimen type 204 and/or one or more additional tissue specimen types included in one or more foreground tiles that were not included in recorded tissue specimen type 204. Notification 224 may be provided for display in conjunction with digital whole slide image 202 through the user interface of viewing application tool 108 to prompt the user (e.g., the pathologist) to review locations or regions of digital whole slide image 202 corresponding to second subset of foreground tiles 208B, and if necessary, correct or remedy recorded tissue specimen type 204 associated with digital whole slide image 202 in laboratory information system 125. In some examples, notification 224 may include graphical and/or textual indications or alerts displayed in association with (e.g., overlaid on) second subset of foreground tiles 208B within digital whole slide image 202.

In further examples, when a discrepancy is determined, second subset of foreground tiles 208B may be prevented from being processed by AI image processing system 220 that is specific to recorded tissue specimen type 204 to avoid erroneous results. Instead, second subset of foreground tiles 208B may be provided to one or more different AI image processing systems that are specific to one or more tissue specimen types identified by predictions 216.

In other aspects, rather than performing the comparison at step 218, each of foreground tiles 208 may be provided as input to a respective AI image processing system that is specific to a tissue specimen type identified as being included in the foreground tile by predictions 216. In other words, predictions 216 may be used to select an appropriate one or more AI image processing systems to be run on foreground tiles 208 of digital whole slide image 202.

Using Unsupervised Learning for Out-of-Distribution Detection

According to one example aspect, the machine learning system used for predicting the one or more tissue specimen types present in the whole slide image may be an unsupervised machine learning system. For an unsupervised machine learning system, the tissue specimen types in the whole slide images received as training images may not be explicitly stated during a learning process (e.g., corresponding annotations or labels identifying the tissue specimen types in the training images are not received and/or used in the learning process). In some examples, unsupervised learning may be implemented with training datasets that are of a single tissue specimen type or of a set of tissue specimen types, where an assumption that the majority of the tissue specimen is of the valid tissue specimen type(s) may be made.

Figure 3A:
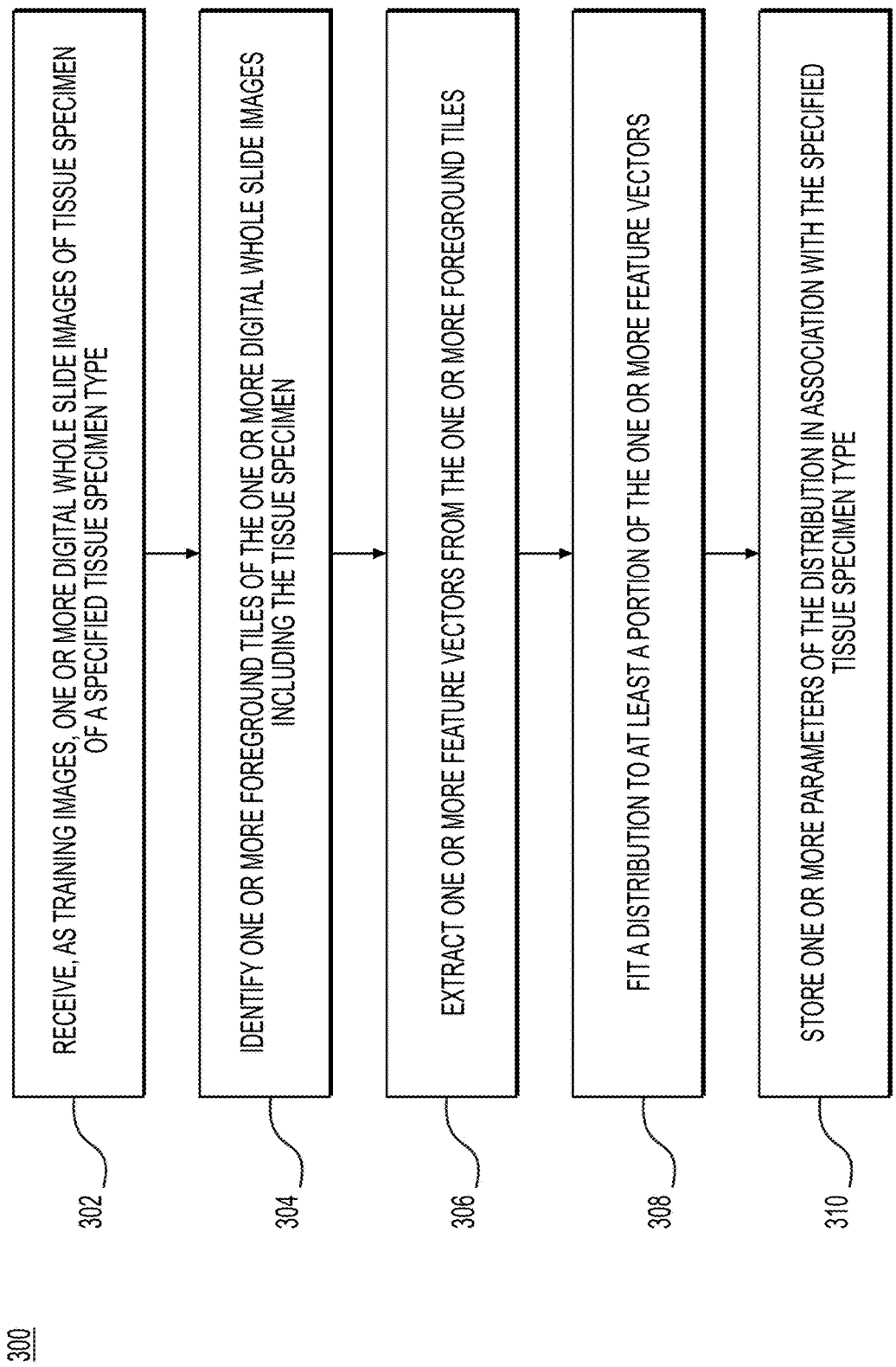
FIG. 3A is a flowchart illustrating an exemplary method for training an unsupervised machine learning system to identify one or more tissue specimen types present in a digital whole slide image, according to an exemplary embodiment of the present disclosure.

FIG. 3A is a flowchart illustrating an exemplary method 300 for training an unsupervised machine learning system to identify one or more tissue specimen types present in a digital whole slide image, according to an exemplary embodiment of the present disclosure. Exemplary method 300 (e.g., steps 302-310) may be performed by training image platform 131 of slide analysis tool 101. Exemplary method 400 may include one or more of the following steps.

In step 302, method 300 may include receiving, as training images, one or more digital whole slide images of tissue specimen of a specified tissue specimen type. For example, the training images may include a single tissue specimen type or of a set of tissue specimen types. Each of the digital whole slide images may be comprised of a plurality of tiles, including foreground tiles and background tiles, and each of the tiles may be comprised of a plurality of pixels. The foreground tiles may be the locations or regions of the digital whole slide image including the tissue specimen.

In step 304, method 300 may include identifying one of more foreground tiles of the one or more whole slide images including the tissue specimen. The foreground tiles may be identified using example image processing techniques described above in detail with reference to step 206 of process 200 in FIG. 2.

In step 306, method 300 may include extracting one or more feature vectors from the one or more foreground tiles. For example, a feature vector may be extracted for each of the foreground tiles. The feature vectors may be extracted using one or more of example image processing techniques and/or machine learning techniques described above in detail with reference to step 210 of process 200 in FIG. 2.

In step 308, method 300 may include fitting a distribution to at least a portion of the one or more feature vectors. One or more of a mixture model, a multivariate Gaussian process, or a Parzen window density estimation (also known as a kernel density estimation), among other similar techniques, may be implemented to fit the distribution. In step 310, method 300 may include storing one or more parameters of the distribution in association with the specified tissue specimen type (e.g., in storage devices 109).

Distributions may be generated for a plurality of different tissue specimen types using the steps of method 300 described above and stored in association with the respective tissue specimen types in storage devices 109, for example.

Figure 3B:
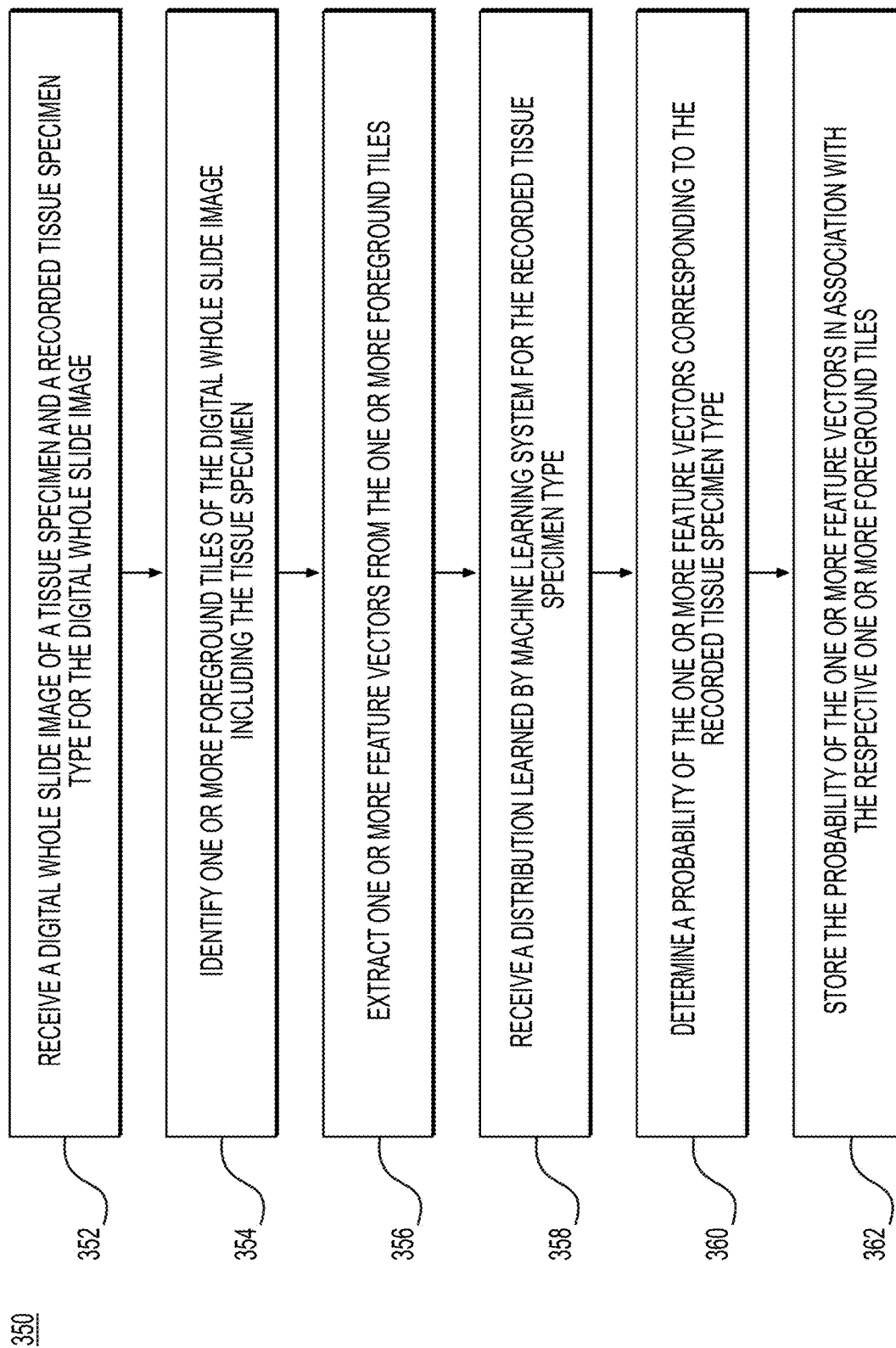
FIG. 3B is a flowchart illustrating an exemplary method for using an unsupervised machine learning system to identify one or more tissue specimen types present in a digital whole slide image, according to an exemplary embodiment of the present disclosure.

FIG. 3B is a flowchart illustrating an exemplary method 350 for using an unsupervised machine learning system to identify one or more tissue specimen types present in a digital whole slide image, according to an exemplary embodiment of the present disclosure. Exemplary method 350 (e.g., steps 352-362) may be performed by target image platform 136 of slide analysis tool 101. Exemplary method 350 may include one or more of the following steps.

In step 352, method 350 may include receiving a digital whole slide image of a tissue specimen and a recorded tissue specimen type for the digital whole slide image. The digital whole slide image may be a digitized image of a slide-mounted tissue specimen received from physician servers 121, hospital servers 122, clinical trial servers 123, research lab servers 124 and/or laboratory information systems 125 and stored in one of storage devices 109. The recorded tissue specimen type may be obtained from data received in association with the digital whole slide image (e.g., from tissue type information recorded in laboratory information systems 125 or other similar database). The digital whole slide image may be comprised of a plurality of tiles, including foreground tiles and background tiles, and each of the tiles may be comprised of a plurality of pixels. The foreground tiles may include the locations or regions of the whole slide image including the tissue specimen.

In step 354, method 350 may include identifying the one of more foreground tiles of the digital whole slide image including the tissue specimen. The foreground tiles may be identified using example image processing techniques described above in detail with reference to step 206 of process 200 in FIG. 2.

In step 356, method 350 may include extracting one or more feature vectors from the one or more foreground tiles. For example, a feature vector may be extracted from each of the one or more foreground tiles. The feature vectors may be extracted using one or more of example image processing techniques and/or machine learning techniques described above in detail with reference to step 210 of process 200 in FIG. 2.

In step 358, method 350 may include receiving a distribution learned by a machine learning system for the recorded tissue specimen type. As one example, one or more of storage devices 109 may store a plurality of distributions in association with a plurality of different tissue specimen types for which the distributions were learned by a machine learning system using unsupervised learning techniques described with reference to method 300 of FIG. 3A. The recorded tissue specimen type may be used to query the storage devices 109, for example, to identify and obtain a distribution that was learned for the recorded tissue specimen type.

In step 360, method 350 may include determining a probability of the one or more feature vectors corresponding to the recorded tissue specimen type using the distribution. For example, a probability for each feature vector may be determined that indicates a likelihood that the tissue specimen included in the respective foreground tile from which the feature vector is extracted is of the recorded tissue specimen type. In some aspects, a predefined threshold (e.g., a predefined probability value) may be used to classify the respective foreground tile from which the feature vector is extracted as an in-distribution foreground tile or an out-of-distribution foreground tile. For example, if the probability determined for the feature vector meets or exceeds the predefined threshold, the respective foreground tile from which the feature vector is extracted may be classified as an in-distribution foreground tile. Classifying the respective foreground tile as an in-distribution foreground tile may indicate that the tissue specimen within the respective foreground tile is of the recorded tissue specimen type. Alternatively, if the probability of the feature vector is below the predefined threshold, the respective foreground tile from which the feature vector is extracted may be classified as an out-of-distribution foreground tile. Classifying the respective foreground tile as an out-of-distribution foreground tile may indicate that the tissue specimen within the respective foreground tile is not of the tissue specimen type recorded for the digital whole slide image.

In step 362, method 350 may include storing the probability of the one or more feature vectors type in association with the respective one or more foreground tiles from which the feature vectors are extracted.

In some examples, the digital whole slide image may be displayed through a user interface of viewing application tool 108. Additionally, the probabilities indicating the likelihood that the tissue specimen included in the foreground tiles is of the recorded tissue specimen type may be displayed in association with the respective foreground tiles (e.g. overlaid on the displayed digital whole slide image). The probability may be displayed as a percentage, a fraction, a decimal, or other similar mathematical format based on the value of the probability determined. In other examples, the probability may be visually displayed in a binary manner as being either above or below the predefined threshold. In further examples, the probability may only be displayed if it is below the predefined threshold to prompt the user (e.g., the pathologist) to review that particular out-of-distribution foreground tile. Additionally or alternatively, when the probability is below the predefined threshold, the foreground tile may be otherwise labeled or indicated as an outlier or an out-of-distribution foreground tile. The indication may be provided as a notification and/or alert through the user interface of viewing application tool 108.

In further examples, an AI image processing system indicated for this digital whole slide image (e.g., a system specific to the recorded tissue specimen type) may be subsequently run on the in-distribution foreground tiles to produce diagnostic outputs for pathology data contained within the in-distribution foreground tiles, e.g., to determine a presence and/or type of a disease or condition, if any. Correspondingly, an instruction to not run the AI system on the out-of-distribution foreground tile(s) may be generated and provided.

Using Supervised Learning with Strong Annotations or Multiple Instance Learning Techniques According to another example aspect, the machine learning system used for predicting the one or more tissue specimen types present in the digital whole slide image may be a supervised machine learning system. In some examples, the supervised machine learning system may be trained using strong annotations in which a tissue specimen type for a tissue specimen included in each pixel (if any) of a plurality of pixels in a training image is labeled (e.g., tissue specimen type is labeled at a pixel level). In other examples, the supervised machine learning system may be trained using multiple-instance learning techniques that employ weak annotations in which tissue specimen type for a training image is labeled at an image or part specimen level.

Figure 4A:
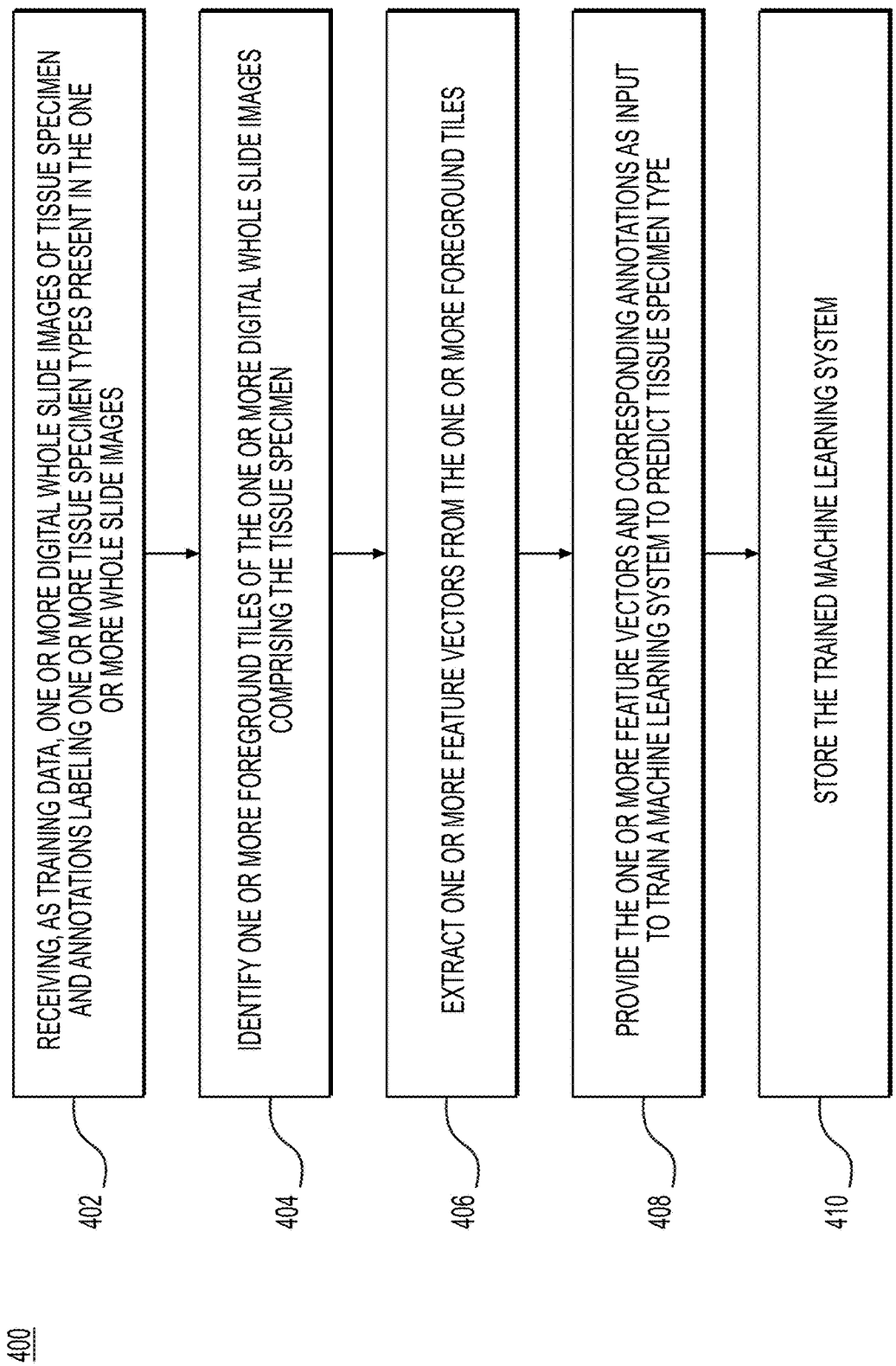
FIG. 4A is a flowchart illustrating an exemplary method for training a supervised machine learning system to identify one or more tissue specimen types present in a digital whole slide image, according to an exemplary embodiment of the present disclosure.

FIG. 4A is a flowchart illustrating an exemplary method 400 for training a supervised machine learning system to identify one or more tissue specimen types present in a digital whole slide image, according to an exemplary embodiment of the present disclosure. Exemplary method 400 (e.g., steps 402-410) may be performed by training image platform 131 of slide analysis tool 101. Exemplary method 400 may include one or more of the following steps.

In step 402, method 400 may include receiving, as training data, one or more digital whole slide images of tissue specimen and annotations labeling one or more tissue specimen types present in the one or more whole slide images. The whole slide images may be training images comprised of a plurality of pixels and the annotations may serve, among other things, as corresponding labels. In some examples, the annotations may be strong annotations, where each of the plurality of pixels in a given training image may be labeled with a corresponding known tissue specimen type of the tissue specimen included in the respective pixel, if any (e.g., labeling occurs at the pixel level). The annotations may be specified using polygons or pixel masks, among other similar examples. In other examples, the annotations may be weak annotations that label whether a given tissue type is present or not within the training image generally (e.g., may be labeled at an image or part specimen level).

In step 404, method 400 may include identifying one or more foreground tiles of the one or more whole slide images comprising the tissue specimen. In some aspects, the identification may be based at least in part on the annotations such that the foreground tiles comprising the tissue specimen that is annotated with a tissue specimen type is identified. For example, foreground tiles including tissue specimen may be identified using example image processing techniques described above in detail with reference to step 206 of process 200 in FIG. 2. Then, of those identified foreground tiles, a subset of the foreground tiles including the tissue specimen having a tissue specimen type annotation may be used in the following steps.

In step 406, method 400 may include extracting one or more feature vectors from the one or more foreground tiles. For example, a feature vector may be extracted for each of the foreground tiles. The feature vectors may be extracted using one or more of example image processing techniques and/or machine learning techniques described above in detail with reference to step 210 of process 200 in FIG. 2.

In step 408, method 400 may include providing the one or more feature vectors and corresponding annotations as input to train a machine learning system to predict tissue specimen type. The machine learning system may be a classification-based system (e.g., a classifier) trained to predict the tissue specimen type using supervised learning.

In some examples, the supervised machine learning system may be trained using strong annotations (e.g. pixel level labels). In such examples, the supervised machine learning system may include a convolutional neural network (CNN), a multi-layer perceptron (MLP), a support vector machine (SVM), a nearest neighbor algorithm model, or a random forest algorithm model, among other similar examples. To enable learning, a feature vector extracted from an identified foreground tile of a training image may be provided as input to the machine learning system. The machine learning system may then output one or more predicted tissue specimen types of the tissue specimen included in the foreground tile. The predicted tissue type(s) may be compared to a corresponding label to determine a loss or error. The corresponding label may be a portion of a strong annotation of the training image that corresponds to the foreground tile and indicates known tissue specimen type(s) present in each of the pixels of the foreground tile. The machine learning system may be modified or altered (e.g., weights and/or bias associated with one or more nodes and/or layers may be adjusted) based on the error to improve an accuracy of the machine learning system. This process may be repeated for each of the foreground tiles identified from each of the training images received or at least until a determined loss or error is below a predefined threshold. In some examples, a portion of the training images may with withheld and used to further validate or test the machine learning system.

In other examples, the supervised machine learning system may be trained using MIL and weak annotations (e.g., labels at an image or part specimen level). For example, when MIL is used, the machine learning system receives a set of "bags", each including a plurality of "instances". Specifically, each of the training images may be described as a "bag" and extracted feature vectors from identified foreground tiles of the respective training image may be the "instances" included in the "bag". A weak annotation may be associated with the "bag". For example, a training image may be labeled as positive for a given tissue specimen type if at least one of the feature vectors included in the training image is indicative of the given tissue specimen type. To learn, the machine learning system may identify the at least one feature vector that is common across training images labeled as positive for the given tissue specimen type. Once trained, the machine learning system may then predict unlabeled, digital whole slide images as including the given tissue specimen type when the common feature vector(s) are identified.

In step 410, method 400 may include storing the trained machine learning system for subsequent use. For example, parameters of the classifier may be stored in storage devices 109.

Figure 4B:
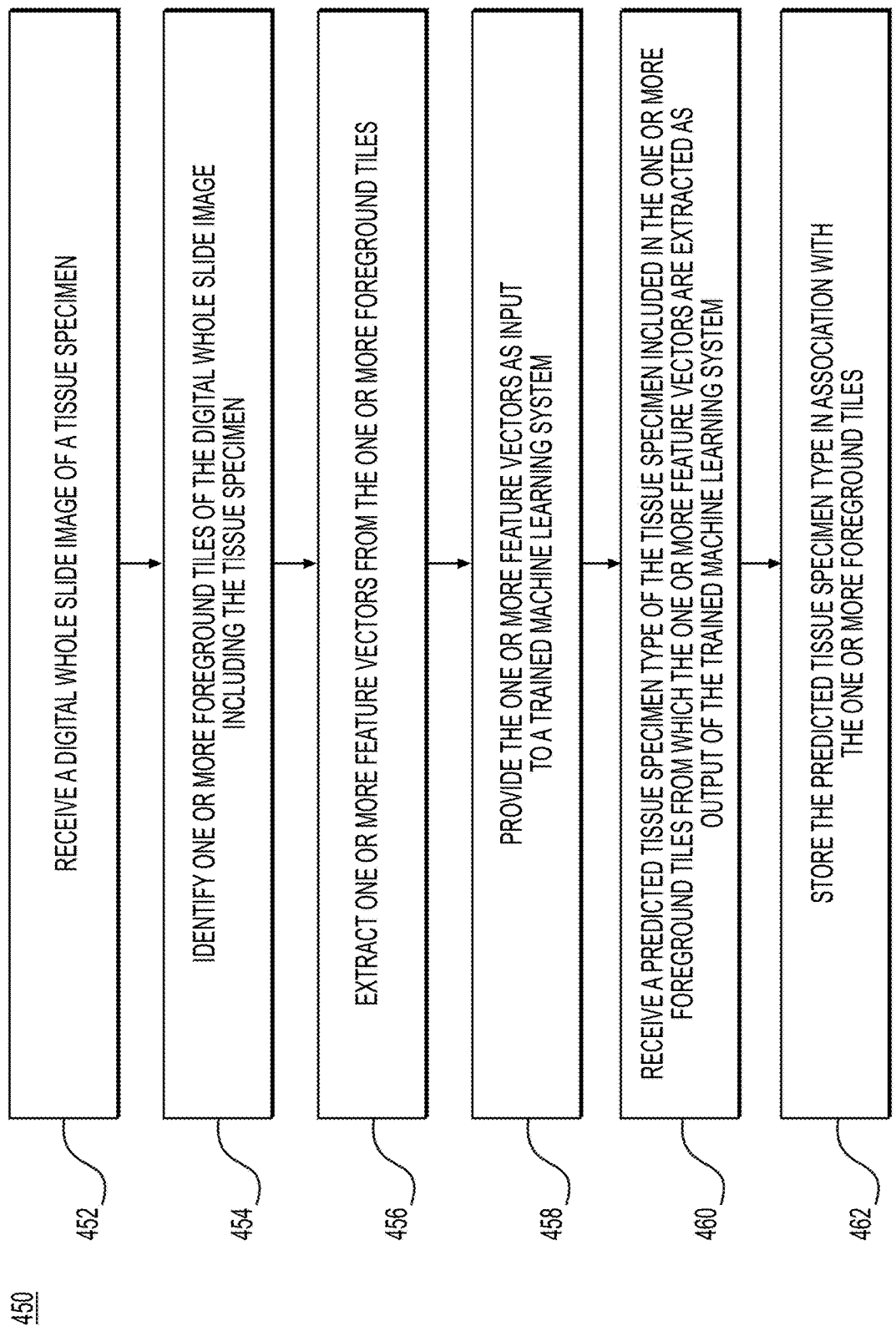
FIG. 4B is a flowchart illustrating an exemplary method for using a supervised machine learning system to identify one or more tissue specimen types present in a digital whole slide image, according to an exemplary embodiment of the present disclosure.

FIG. 4B is a flowchart illustrating an exemplary method 450 for using a supervised machine learning system to identify one or more tissue specimen types present in a digital whole slide image. Exemplary method 450 (e.g., steps 452-462) may be performed by target image platform 136 of slide analysis tool 101. Exemplary method 450 may include one or more of the following steps.

In step 452, method 450 may include receiving a digital whole slide image of a tissue specimen. In some examples, the recorded tissue specimen type for the digital whole slide image may be optionally received from laboratory information system 125 and/or or other similar database for the given whole slide image.

In step 454, method 450 may include identifying one or more foreground tiles of the digital whole slide image including the tissue specimen. The foreground tiles may be identified using example image processing techniques described above in detail with reference to step 206 of process 200 in FIG. 2.

In step 456, method 450 may include extracting one or more feature vectors from the one or more foreground tiles. For example, a feature vector may be extracted for each of the foreground tiles. The feature vectors may be extracted using one or more of example image processing techniques and/or machine learning techniques described above in detail with reference to step 210 of process 200 in FIG. 2.

In step 458, method 450 may include providing the one or more feature vectors as input to a trained machine learning system. The trained machine learning system may be a supervised machine learning system, such as one of the supervised machine learning systems trained in accordance with steps 402-410 of method 400 described above with reference to FIG. 4A.

In step 460, method 450 may include receiving a predicted tissue specimen type of the tissue specimen included in the one or more foreground tiles from which the one or more feature vectors are extracted as output of the trained machine learning system. For example, a predicted tissue specimen type included in each foreground tile may be received, resulting in a predicted one or more tissue specimen types collectively present in the digital whole image. In step 462 of method 450, method 450 may include storing the predicted tissue specimen type in association with the one or more foreground tiles of the digital whole slide image (e.g., in storage devices 109).

In some examples, the digital whole slide image may be displayed through a user interface of viewing application tool 108. Additionally, the predicted tissue specimen type may be displayed as a specimen type classification in association with the respective foreground tiles.

In other aspects, when the recorded tissue specimen type for the digital whole slide image is received (e.g., from laboratory information system 125), a comparison may be performed between the predicted tissue specimen type(s) and the recorded tissue specimen type. If there is a discrepancy (e.g., a mismatch and/or one or more additional tissue specimen types are predicted as being present), a notification and/or alert may be provided through the user interface of viewing application tool 108 to prompt review and resolution.

In further aspects, based on the predicted tissue specimen type, each foreground tile may be provided as input to a corresponding AI image processing system that is specific to the tissue specimen type predicted for that foreground tile for processing. In some examples, the AI image processing system may produce diagnostic outputs for pathology data contained within the foreground tiles, e.g., to determine a presence and/or type of a disease or condition, if any.

Example Applications for the Systems and Methods

Techniques presented herein for predicting one or more tissue specimen types present in a digital whole slide image may be implemented in a variety of applications. Exemplary non-limiting, non-exhaustive applications are described below with reference to FIGS. 5, 6, and 7.

Example Embodiment: Floater Detection

Figure 5:
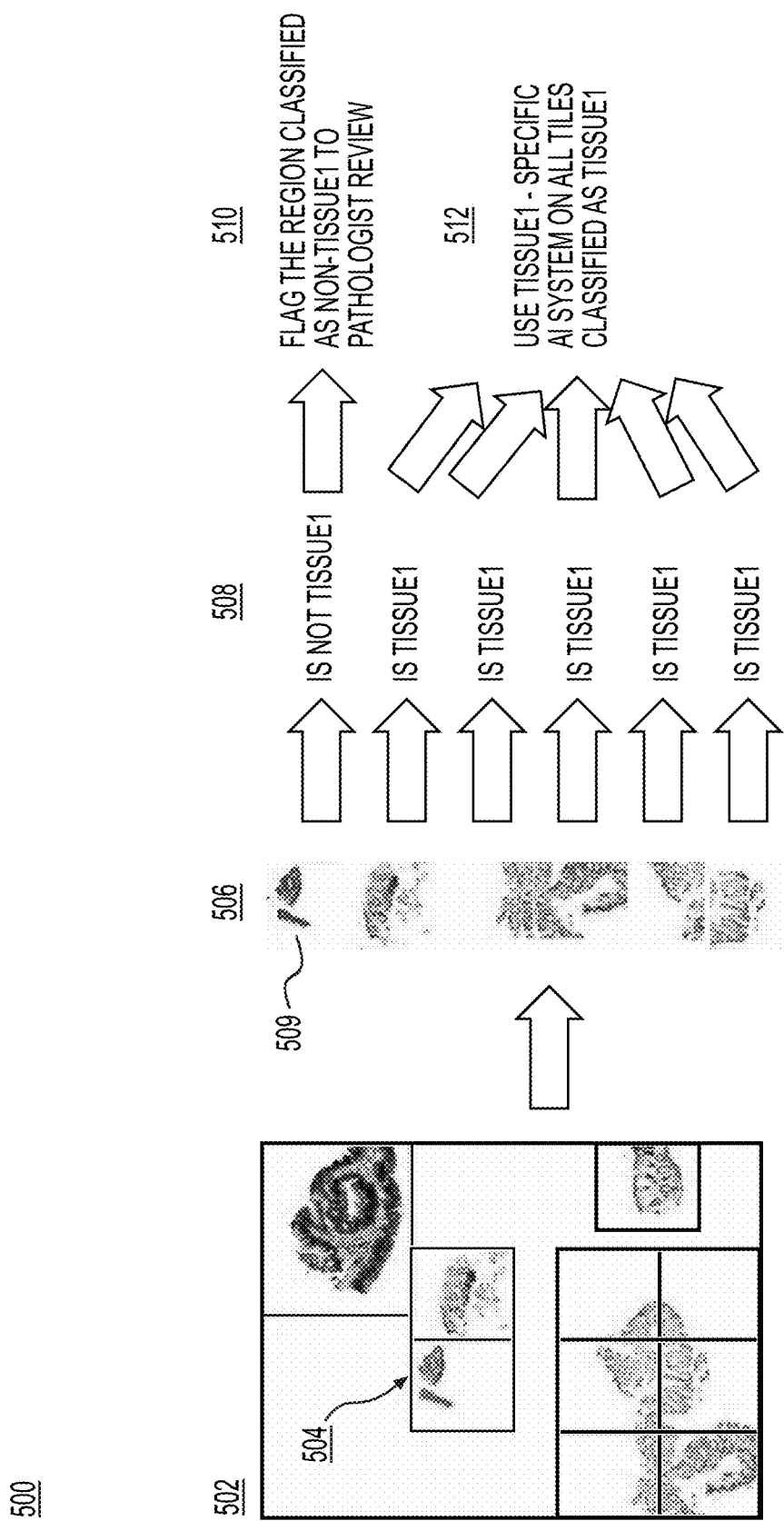
FIG. 5 is a conceptual diagram illustrating an exemplary application of a tissue classification platform for floater detection, according to an exemplary embodiment of the present disclosure.

FIG. 5 is a conceptual diagram 500 illustrating an exemplary application of tissue classification platform 100 for floater detection, according to an exemplary embodiment of the present disclosure. An example digital whole slide image 502 of a tissue specimen of a specified type (e.g., of a first tissue specimen type) may also include a floater 504. Floater 504 may be a foreign piece of tissue that, when present in digital whole slide image 502 and processed by an AI image processing system specific to the first tissue specimen type to yield diagnostic outputs, may result in an incorrect diagnosis. To prevent such incorrect diagnosis, tissue classification platform 100 may be applied to identify and distinguish between locations or regions of digital whole slide image 502 comprising the first tissue specimen type and the floater such that AI image processing system only process the locations or regions of digital whole slide image 502 comprising the first tissue specimen type.

Specifically, slide analysis tool 101 of tissue classification platform 100 may perform a same or similar process to process 200 described above with reference to FIG. 2. For example, digital whole slide image 502 may be received along with a list of expected tissue specimen types present within digital whole slide image 502 (e.g., an example of a recorded tissue specimen type). In this illustrative example, the expected tissue specimen types may include first tissue specimen type ("Tissue1"). Foreground tiles 506 of digital whole slide image 502 including the tissue specimen may be identified. A feature vector may be extracted from each of foreground tiles 506 and provided as input to a trained machine learning system to receive, as output, predictions 508 associated with one or more tissue specimen types included in the respective foreground tiles.

Based on predictions 508, the foreground tile comprising floater 504 (e.g., foreground tile 509) may be identified as not including the first tissue specimen type or as including a different tissue specimen type. When comparing predictions 508 to the tissue specimen types included in the list, foreground tile 509 may further be classified as including an unexpected tissue specimen type. Additionally, a location or region of digital whole slide image 502 corresponding to foreground tile 509 may be flagged or otherwise indicated to prompt a user (e.g., a pathologist) to review at process 510. Further, based on predictions 508 indicating that remaining foreground tiles (e.g., foreground tiles 506 other than foreground tile 509) include the first tissue specimen type as expected, these remaining foreground tiles may be provided as input to the AI image processing system specific to the first tissue specimen type to yield diagnostic outputs at process 512.

Example Embodiment: Determining AI System to Use

Figure 6:
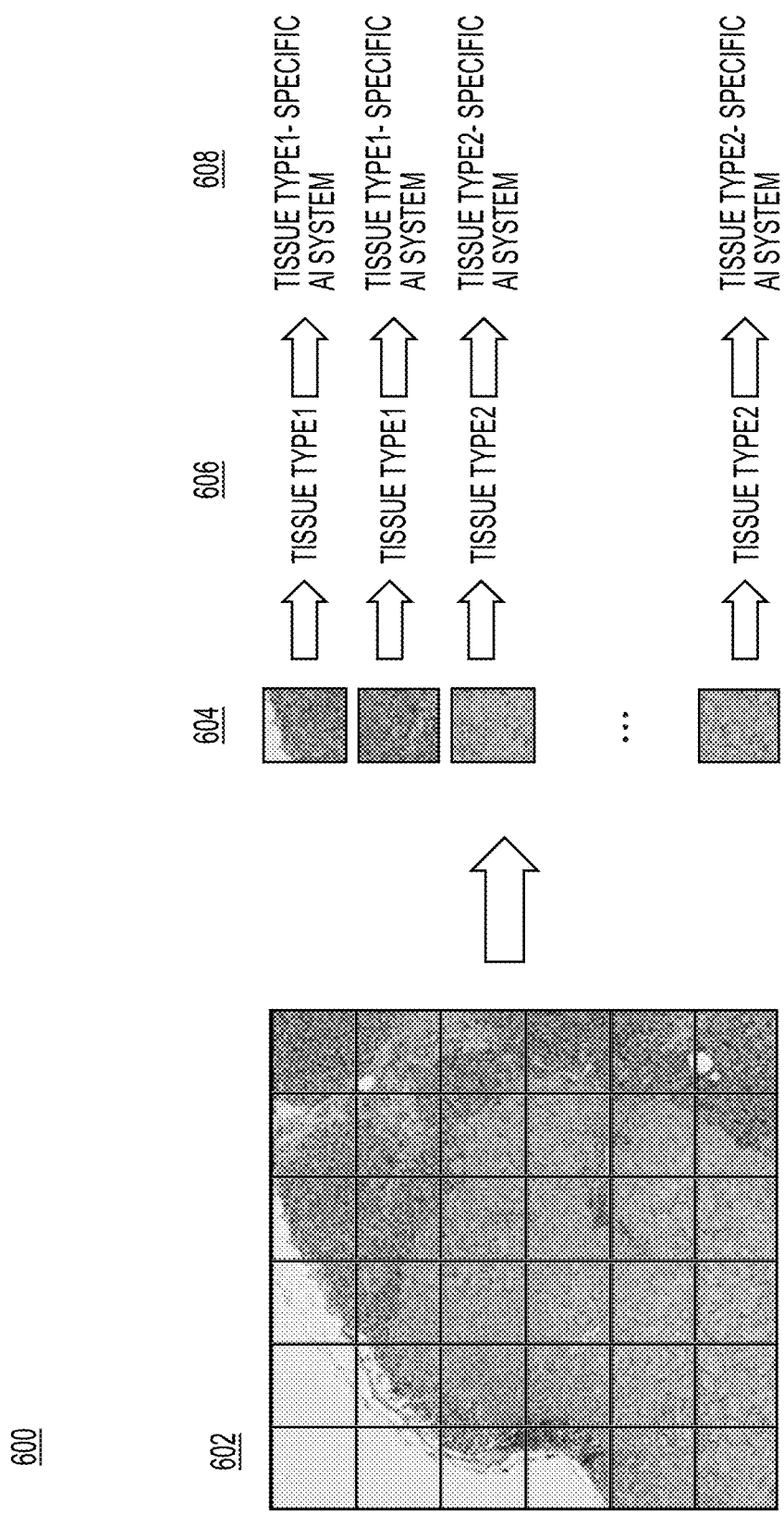
FIG. 6 is a conceptual diagram illustrating an exemplary application of a tissue classification platform for determining an AI-based image processing system to subsequently apply to a digital whole slide image, according to an exemplary embodiment of the present disclosure.

FIG. 6 is a conceptual diagram 600 illustrating an exemplary application of tissue classification platform 100 for determining an AI-based image processing system to subsequently apply to a digital whole slide image 602, according to an exemplary embodiment of the present disclosure. To provide an illustrative example, a patient may have a tumor, such as a breast tumor excised along with one or more lymph nodes to identify metastasis, and a slide may be prepared that contains both the breast tumor and lymph nodes. Accordingly, a digitized image of the slide (e.g., a digital whole slide image 602) may include two different tissue specimen types, "Tissue Type1" comprising breast tissue and "Tissue Type2" comprising lymphoid tissue.

To identify the locations or regions of digital whole slide image 602 corresponding to each of the different tissue specimen types, slide analysis tool 101 of tissue classification platform 100 may perform a same or similar process to process 200 described above with reference to FIG. 2. For example, upon receiving digital whole slide image 602, foreground tiles 604 of digital whole slide image 602 including the tissue specimen may be identified. A feature vector may be extracted from each of foreground tiles 604 and provided as input to a trained machine learning system to receive, as output, predictions 606 associated with one or more tissue specimen types of the tissue specimen included in the respective foreground tiles 604. For example, based on predictions 606, a first portion of foreground tiles 604 may include breast tissue (e.g., "Tissue Type1") and a second portion of foreground tiles 604 may include lymphoid tissue (e.g., "Tissue Type2").

At process 608, the first portion and second portion of foreground tiles 604 may be provided as input to a corresponding AI image processing system that is specific to the respective tissue specimen types. For example, the first portion of foreground tiles 604 may be provided as input to a first AI image processing system specific to breast tissue to yield diagnostic outputs, and the second portion of foreground tile 604 may be provided as input to a second AI image processing system specific to lymphoid tissue to yield accurate diagnostic outputs.

Figure 7:
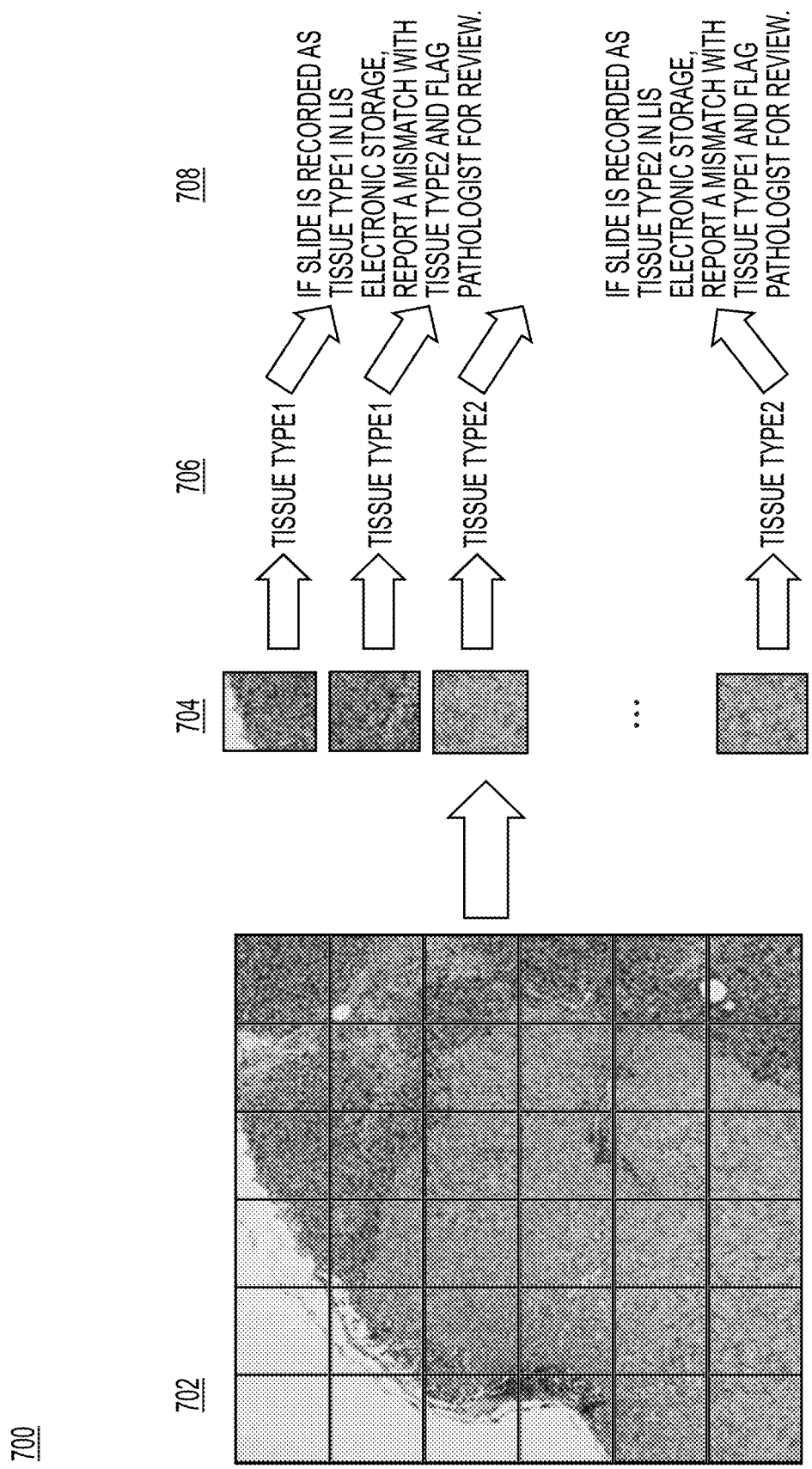
FIG. 7 is a conceptual diagram illustrating an exemplary application of a tissue classification platform for detecting errors in a laboratory information system, according to an exemplary embodiment of the present disclosure.

Example Embodiment: Detecting Errors in Laboratory Information System Classification FIG. 7 is a conceptual diagram 700 illustrating an exemplary application of tissue classification platform 100 for detecting errors in a laboratory information system (e.g., laboratory information system 125), according to an exemplary embodiment of the present disclosure.

Slide analysis tool 101 of tissue classification platform 100 may perform the same or similar process 200 described above with reference to FIG. 2. For example, a digital whole slide image 702 of a tissue specimen may be received along with a recorded tissue specimen type for digital whole slide image 702 from laboratory information system 125 or similar other database. Foreground tiles 704 of digital whole slide image 702 including the tissue specimen may be identified. A feature vector may be extracted from each of foreground tiles 704 and provided as input to a machine learning system to receive, as output, predictions 706 associated with one or more tissue specimen types present in the respective foreground tiles. At comparison process 708, predictions 706 may be compared to the recorded tissue specimen type for digital whole slide image 702, where if the predicted tissue specimen type for a given foreground tile 704 does not align with or match the recorded tissue specimen type (e.g., there is a discrepancy), the discrepancy may be reported and/or stored in association with digital whole slide image 702 and the given foreground tile 704 may be flagged or otherwise indicated to prompt a user (e.g., a pathologist) to review. For example, if the recorded tissue specimen type for digital whole slide image 702 in laboratory information system 125 is a first tissue specimen type (e.g., "Tissue Type1"), then, for any foreground tiles 704 for which predictions 706 indicated a second tissue specimen type (e.g., "Tissue Type2"), the discrepancy is reported and/or stored and those foreground tiles 704 are flagged for review. On the other hand, if the recorded tissue specimen type is the second tissue specimen type (e.g., "Tissue Type2"), then, for any foreground tiles 704 for which predictions 706 indicated first tissue specimen type (e.g., "Tissue Type1"), the discrepancy is reported and/or stored and those foreground tiles 704 are flagged for review.

Figure 8:
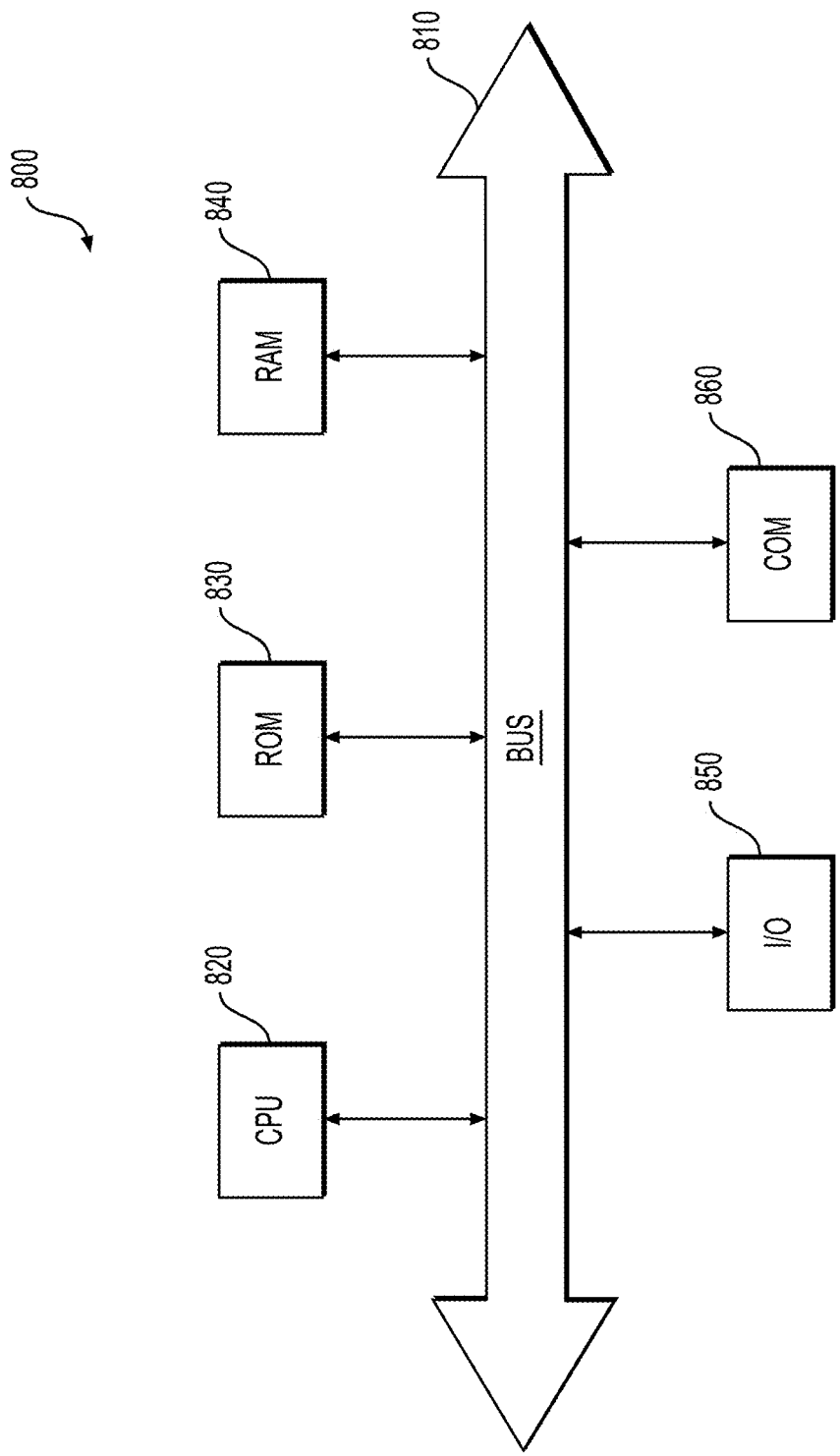
FIG. 8 illustrates an example system that may execute techniques presented herein.

FIG. 8 illustrates an example system or device 800 that may execute techniques presented herein. Device 800 may include a central processing unit (CPU) 820. CPU 820 may be any type of processor device including, for example, any type of special purpose or a general-purpose microprocessor device. As will be appreciated by persons skilled in the relevant art, CPU 820 also may be a single processor in a multi-core/multiprocessor system, such system operating alone, or in a cluster of computing devices operating in a cluster or server farm. CPU 820 may be connected to a data communication infrastructure 810, for example a bus, message queue, network, or multi-core message-passing scheme.

Device 800 may also include a main memory 840, for example, random access memory (RAM), and also may include a secondary memory 830. Secondary memory 830, e.g. a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 830 may include similar means for allowing computer programs or other instructions to be loaded into device 800. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 800.

Device 800 also may include a communications interface ("COM") 860. Communications interface 860 allows software and data to be transferred between device 800 and external devices. Communications interface 860 may include a modem, a network interface (such as an Ethernet card), a communications port, a PCMCIA slot and card, or the like. Software and data transferred via communications interface 860 may be in the form of signals, which may be electronic, electromagnetic, optical or other signals capable of being received by communications interface 860. These signals may be provided to communications interface 860 via a communications path of device 800, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 800 may also include input and output ports 850 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments may be apparent to those skilled in the art from consideration of the specification and practice of the invention disclosed herein. It is intended that the specification and examples be considered as exemplary only.

What is claimed is:

1. A system for identifying one or more tissue specimen types by processing electronic images, the system comprising:
   a processor; and
   a memory coupled to the processor and storing instructions that, when executed by the processor, cause the system to perform operations comprising:
      receiving, from a data store, a digital whole slide image of a tissue specimen and a recorded tissue specimen type for the digital whole slide image that is stored in association with the digital whole slide image in the data store;
      identifying one or more foreground tiles of the digital whole slide image that include the tissue specimen;
      extracting one or more feature vectors from the one or more foreground tiles;
      providing the one or more feature vectors as input to a trained machine learning system;
      receiving a predicted tissue specimen type of the tissue specimen included in each of the one or more foreground tiles from which the one or more feature vectors are extracted as output of the trained machine learning system;
      comparing the predicted tissue specimen type to the recorded tissue specimen type; and
      for each of the one or more foreground tiles, providing the respective foreground tile to a first image processing system specific to the recorded tissue specimen type when there is an alignment between the predicted specimen type and the recorded tissue specimen type based on the comparing, and providing the respective foreground tile to a second image processing system different from the first image processing system that is specific to the predicted tissue specimen type when there is a discrepancy between the predicted specimen type and the recorded tissue specimen type based on the comparing.

2. The system of claim 1, wherein, when there is a discrepancy between the predicted specimen type of the tissue specimen included in the respective foreground tile and the recorded tissue specimen type based on the comparing, the operations further comprising:
   generating and providing for display a notification indicating the discrepancy.

3. The system of claim 2, the operations further comprising:
   providing the digital whole slide image for display, wherein the notification is displayed in association with the respective foreground tile within the displayed digital whole image.

4. The system of claim 1, wherein the discrepancy includes one or more of:
   a mismatch between the predicted tissue specimen type of the tissue specimen included in the respective foreground tile and the recorded tissue specimen type, or
   an additional predicted tissue specimen type not included in the recorded tissue specimen type.

5. The system of claim 1, wherein the trained machine learning system is a supervised machine learning system that is trained using strong annotations by:
   receiving, as training data, one or more digital whole slide images of tissue specimen and strong annotations labeling a tissue specimen type included in each pixel of the one or more digital whole slide images;
   identifying one or more foreground tiles of the one or more digital whole slide images including the tissue specimen;
   extracting one or more feature vectors from the one or more foreground tiles; and
   providing the one or more feature vectors and corresponding strong annotations as input to train the supervised machine learning system to predict tissue specimen type.

6. The system of claim 5, wherein the supervised machine learning system includes at least one of a convolutional neural network (CNN), a multi-layer perceptron (MLP), a support vector machine (SVM), a nearest neighbor algorithm model, or a random forest algorithm model.

7. The system of claim 1, wherein the trained machine learning system is a supervised machine learning system that is trained using multiple instance learning by:
   receiving, as training data, a set of one or more digital whole slide images of tissue specimen including at least one tissue specimen type and weak annotations labeling the at least one tissue specimen type as being present at an image level or tissue specimen level;

identifying one or more foreground tiles of the one or more digital whole slide images including the tissue specimen;

extracting one or more feature vectors from the one or more foreground tiles; and providing the one or more feature vectors and the weak annotations as input to train the supervised machine learning system to predict tissue specimen type, wherein the supervised machine learning system learns at least one common feature vector among the set that is representative of the at least one tissue specimen type.

8. The system of claim 1, the operations further comprising:

providing for display the digital whole slide image and the predicted tissue specimen type of the tissue specimen included in each of the one or more foreground tiles, the predicted tissue specimen type being displayed in association with the respective one or more foreground tiles.

9. The system of claim 1, wherein the first image processing system is trained to process the respective foreground tile to predict a diagnosis associated with the recorded tissue specimen type.

10. The system of claim 1, wherein the second image processing system is trained to process the respective foreground tile to predict a diagnosis associated with the predicted tissue specimen type when there is a discrepancy between the predicted tissue specimen type and the recorded tissue specimen type.

11. A method for identifying one or more tissue specimen types by processing electronic images, the method comprising:

receiving, from a data store, a digital whole slide image of a tissue specimen and a recorded tissue specimen type for the digital whole slide image that is stored in association with the digital whole slide image in the data store;

identifying one or more foreground tiles of the digital whole slide image that include the tissue specimen;

extracting one or more feature vectors from the one or more foreground tiles;

providing the one or more feature vectors as input to a trained machine learning system;

receiving a predicted tissue specimen type of the tissue specimen included in each of the one or more foreground tiles from which the one or more feature vectors are extracted as output of the trained machine learning system;

comparing the predicted tissue specimen type to the recorded tissue specimen type; and for each of the one or more foreground tiles, only providing the respective foreground tile to an image processing system for processing when there is an alignment between the predicted specimen type and the recorded tissue specimen type based on the comparing.

12. The method of claim 11, wherein the image processing system is specific to the recorded tissue specimen type.

13. The method of claim 11, wherein, for at least one of the one or more foreground tiles, a discrepancy between the predicted tissue specimen type of the tissue specimen included in the at least one foreground tile and the recorded tissue specimen type is determined based on the comparing, and the method further comprises:

generating and providing for display a notification indicating the discrepancy.

14. The method of claim 13, further comprising:
providing the digital whole slide image for display, wherein the notification is displayed in association with the at least one foreground tile within the displayed digital whole image.

15. The method of claim 13, wherein the discrepancy includes one or more of:
a mismatch between the predicted tissue specimen type of the tissue specimen included in the at least one foreground tile and the recorded tissue specimen type, or
an additional predicted tissue specimen type not included in the recorded tissue specimen type.

16. The method of claim 11, wherein the trained machine learning system is a supervised machine learning system that is trained using strong annotations by:

receiving, as training data, one or more digital whole slide images of tissue specimen and strong annotations labeling a tissue specimen type included in each pixel of the one or more digital whole slide images;

identifying one or more foreground tiles of the one or more digital whole slide images including the tissue specimen;

extracting one or more feature vectors from the one or more foreground tiles; and providing the one or more feature vectors and corresponding strong annotations as input to train the supervised machine learning system to predict tissue specimen type.

17. The method of claim 11, wherein the trained machine learning system is a supervised machine learning system that is trained using multiple instance learning by:

receiving, as training data, a set of one or more digital whole slide images of tissue specimen including at least one tissue specimen type and weak annotations labeling the at least one tissue specimen type as being present at an image level or tissue specimen level;

identifying one or more foreground tiles of the one or more digital whole slide images including the tissue specimen;

extracting one or more feature vectors from the one or more foreground tiles; and providing the one or more feature vectors and the weak annotations as input to train the supervised machine learning system to predict tissue specimen type, wherein the supervised machine learning system learns at least one common feature vector among the set that is representative of the at least one tissue specimen type.

18. The method of claim 11, wherein the image processing system is a first processing system, and, for at least one of the one or more foreground tiles, a discrepancy between the predicted tissue specimen type of the tissue specimen included in the at least one foreground tile and the recorded tissue specimen type is determined based on the comparing, and the method further comprises:

providing the at least one foreground tile to a second image processing system different from the first image processing system.

19. A non-transitory computer-readable medium storing instructions that, when executed by a processor, cause the processor to perform operations for identifying one or more tissue specimen types by processing electronic images, the operations comprising:

receiving, from a data store, a digital whole slide image of a tissue specimen and a recorded tissue specimen type for the digital whole slide image that is stored in association with the digital whole slide image in the data store;

identifying one or more foreground tiles of the digital whole slide image that include the tissue specimen;

extracting one or more feature vectors from the one or more foreground tiles;

providing the one or more feature vectors as input to a trained machine learning system;

receiving a predicted tissue specimen type of the tissue specimen included in each of the one or more foreground tiles from which the one or more feature vectors are extracted as output of the trained machine learning system;

comparing the predicted tissue specimen type to the recorded tissue specimen type; and for each of the one or more foreground tiles, providing the respective foreground tile to a first image processing system specific to the recorded tissue specimen type when there is an alignment between the predicted specimen type and the recorded tissue specimen type based on the comparing, and generating and providing for display a notification for the respective foreground tile when there is a discrepancy between the predicted specimen type and the recorded tissue specimen type based on the comparing, the notification indicating the discrepancy.

20. The non-transitory computer-readable medium of claim 19, wherein the image processing system is a first processing system, and, for each of the one or more foreground tiles, when there is a discrepancy between the predicted specimen type and the recorded tissue specimen type based on the comparing, the operations further comprise:

providing the respective foreground tile to a second image processing system different from the first image processing system.

* * * * *